US006153441A

United States Patent [19]
Appelbaum et al.

[11] Patent Number: 6,153,441
[45] Date of Patent: Nov. 28, 2000

[54] METHODS OF SCREENING FOR AGONISTS AND ANTAGONISTS FOR HUMAN CCR7 RECEPTOR AND CKβ-9 LIGAND AND INTERACTION THEREOF

[75] Inventors: Edward R. Appelbaum, Blue Bell; Henry M. Sarau, Harleysville; John R. White, Coatesville, all of Pa.

[73] Assignee: SmithKline Beecham Corporation, Philadelphia, Pa.

[21] Appl. No.: 09/251,545

[22] Filed: Feb. 17, 1999

Related U.S. Application Data

[60] Provisional application No. 60/074,883, Feb. 17, 1998.

[51] Int. Cl.$^7$ .................. G01N 33/566; G01N 33/53; G01N 33/567; C12P 21/06; C12P 21/02
[52] U.S. Cl. .................... 436/501; 435/7.1; 435/7.2; 435/7.21; 435/69.1; 435/69.5
[58] Field of Search .................... 436/501, 6; 435/7.1, 435/69.1, 69.5, 7.2, 7.21

[56] References Cited

U.S. PATENT DOCUMENTS 5,605,817  2/1997  Coleman et al. .

FOREIGN PATENT DOCUMENTS

| WO 94/12519 | 6/1994 | WIPO . |
| WO 94/12635 | 6/1994 | WIPO . |
| WO 96/06169 | 2/1996 | WIPO . |
| WO 96/22374 | 7/1996 | WIPO . |
| WO 96/25497 | 8/1996 | WIPO . |
| WO 98/31809 | 7/1998 | WIPO . |

OTHER PUBLICATIONS

Hedrick, et al., "Identification and Characterization of a Novel β Chemokine Containing Six Conserved Cysteines," *The Journal of Immunology*, 159: pp. 1589–1593 (1997).

Hromas, et al., "Isolation and Characterization of Exodus–2, a Novel C–C Chemokine with a Unique 37–Amino Acid Carboxyl–Terminal Extension," *The Journal of Immunology*, 159: pp. 2554–2558 (1997).

Nagira, et al., "Molecular Cloning of a Novel Human CC Chemokine Secondary Lymphoid–Tissue Chemokine That Is a Potent Chemoattractant for Lymphocytes and Mapped to Chromosome 9p13," *The American Society for Biochemistry and Molecular Biology, Inc.*, 272 (Nov. 31, Issue of Aug. 1, 1997): pp. 19518–19524 (1997).

Li, T. et al, Proc Natl Acad Sci USA 92:8(3551–5), Apr. 1995.

*Primary Examiner*—Elizabeth Kemmerer
*Assistant Examiner*—Michael Brannock
*Attorney, Agent, or Firm*—Elizabeth J. Hecht; William T. King; Charles M. Kinzig

[57] ABSTRACT

Disclosed are methods for discovering agonists and antagonists of the interaction between a secreted human protein, chemokine CKβ-9, and its cellular receptor, human CCR7, which may have utility in the treatment of several human diseases, including, but not limited to: allergic disorders, autoimmune diseases, ischemia/reperfusion injury, development of atherosclerotic plaques, cancer (including mobilization of hematopoietic stem cells for use in chemotherapy or myeloprotection during chemotherapy), chronic inflammatory disorders, chronic rejection of transplanted organs or tissue grafts, chronic myelogenous leukemia, and infection by HIV and other pathogens.

4 Claims, 7 Drawing Sheets

Figure 1. Amino Acid sequence of human CCR7 (also known as EBI1 or BLR2) (SEQ ID NO: 1).

```
  1 MDLGKPMKSV LVVALLVIFQ VCLCQDEVTD DYIGDNTTVD YTLFESLCSK KDVRNFKAWF
 61 LPIMYSIICF VGLLGNGLVV LTYIYFKRLK TMTDTYLLNL AVADILFLLT LPFWAYSAAK
121 SWVFGVHFCK LIFAIYKMSF FSGMLLLLCI SIDRYVAIVQ AVSAHRHRAR VLLISKLSCV
181 GIWILATVLS IPELLYSDLQ RSSSEQAMRC SLITEHVEAF ITIQVAQMVI GFLVPLLAMS
241 FCYLVIIRTL LQARNFERNK AIKVIIAVVV VFIVFQLPYN GVVLAQTVAN FNITSSTCEL
301 SKQLNIAYDV TYSLACVRCC VNPFLYAFIG VKFRNDLFKL FKDLGCLSQE QLRQWSSCRH
361 IRRSSMSVEA ETTTTFSP
```

Figure 2. Amino Acid sequence of human CKβ-9 (also known as SLC, 6Ckine, and exodus-2) (SEQ ID NO: 2).

```
  1 MAQSLALSLL ILVLAFGIPR TQGSDGGAQD CCLKYSQRKI PAKVVRSYRK QEPSLGCSIP
 61 AILFLPRKRS QAELCADPKE LWVQQLMQHL DKTPSPQKPA QGCRKDRGAS KTGKKGKGSK
121 GCKRTERSQT PKGP
```

METHODS OF SCREENING FOR AGONISTS AND ANTAGONISTS FOR HUMAN CCR7 RECEPTOR AND CKβ-9 LIGAND AND INTERACTION THEREOF

CROSS-REFERENCE TO RELATED APPLICATION

This application claims benefit to the earlier provisional U.S. application Ser. No. 60/074,883, filed on Feb. 17, 1998, the contents of which are incorporated herein by reference in their entirety.

FIELD OF INVENTION

This invention relates to methods for discovering agonists and antagonists of the interaction between a secreted human protein, chemokine CKβ-9 (also known as SLC, Exodus-2/6Ckine), and its cellular receptor, CCR7 (also known as EBI1 and BLR2). Such agonists and antagonists are believed to be useful in treating several human diseases/disorders, including, but not limited to: allergic disorders, autoimmune diseases, ischemia/reperfusion injury, development of atherosclerotic plaques, cancer (including mobilization of hematopoictic stem cells for use in chemotherapy or myeloprotection during chemotherapy), chronic inflammatory disorders, chronic rejection of transplanted organs or tissue grafts, chronic myclogenous leukemia, and infection by HIV and other pathogens.

BACKGROUND OF THE INVENTION

Chemokines (chemoattractant cytokines) comprise a family of structurally related secreted proteins of about 70–110 amino acids that share the ability to induce migration and activation of specific types of blood cells (reviewed in Baggiolini M., et al. (1997) *Annu. Rev. inmmunol.* 15: 675–705; Proost P., et al. (1996) *Int. J. Clin. Lab. Rse.* 26: 211–223; Premack, et al. (1996) *Nature Medicine* 2: 1174–1178; Yoshie, et al. (1997) *J. Leukocyte Biol.* 62: 634–644). Over 30 different human chemokines have been described to date. They vary in their specificities for different leukocyte types (neutrophils, monocytes, eosinophils, basophils, lymphocytes, dendritic cells, etc.), and in the types of cells and tissues where the chemokines are synthesized. Chemokines are typically produced at sites of tissue injury or stress, where they promote the infiltration of leukocytes into tissues and facilitate an inflammatory response. Some chemokines act selectively on immune system cells such as subsets of T-cells or B lymphocytes or antigen presenting cells, and may thereby promote immune responses to antigens. Some chemokines also have the ability to regulate the growth or migration of hematopoietic progenitor and stem cells that normally differentiate into specific leukocyte types, thereby regulating leukocyte numbers in the blood.

The activities of chemokines are mediated by cell surface receptors which are members of the family of seven transmembrane, G-protein coupled receptors. At present, over twelve different human chemokine receptors are known, including CCR1, CCR2, CCR3, CCR4, CCR5, CCR6, CCR7, CCR8, CXCR1, CXCR2, CXCR3, and CXCR4. These receptors vary in their specificites for specific chemokines. Some receptors bind to a single known chemokine, while others bind to multiple chemokines. Binding of a chemokine to its receptor typically induces intracellular signaling responses such as a transient rise in cytosolic calcium concentration, followed by cellular biological responses such as chemotaxis. Some chemokine receptors also serve as coreceptors for HIV, such that they interact with HIV and with the cellular CD4 receptor to facilitate viral entry into cells.

Chemokines are important in medicine because they regulate the movement and biological activities of leukocytes in many disease situations, including, but not limited to: allergic disorders, autoimmune diseases, ischemia/reperfusiion injury, development of atherosclerotic plaques, cancer (including mobilization of hematopoietic stem cells for use in chemotherapy or myeloprotection during chemotherapy), chronic inflammatory disorders, chronic rejection of transplanted organs or tissue grafts, chronic myelogenous leukemia, and infection by HIV and other pathogens.

Antagonists of chemokine receptors may be of benefit in many of these diseases by reducing excessive inflammation and immune system responses. In the case of HIV infection, chemokines and antagonists which bind to HIV coreceptors may have utility in inhibiting viral entry into cells. The chemokines themselves, or agonists of their receptors, may also have utility in enhancing leukocyte movements in certain situations, such as mobilization of progenitor or stem cells out of the bone marrow into the bloodstream, where they can be harvested prior to cancer chemotherapy and then later be used to replenish cells killed during chemotherapy.

This invention encompasses the novel discovery that chemokine CKβ-9 uses CCR7 as its receptor. We discovered this receptor/ligand relationship by conducting experiments that show that human CKβ-9 polypeptide (SEQ ID NO: 2) induces calcium mobilization in human CCR7 (SEQ ID NO: 1) cell line. Therefore, this invention enables the screening of compounds that can either agonize or antagonize CKβ-9 and/or CCR7 and interactions thereof. We claim these screening methods and any antagonists and agonists discovered using them. We also disclose the discovery that CKβ-9 is a more potent ligand for CCR7 than is CKβ-11.

Chemokine CKβ-9 (also known as SLC, 6Ckine, and exodus-2) was previously known to be highly expressed in lymphoid tissues at the mRNA level, and to be a chemoattractant for T and B lymphocytes (Nagira, et al. (1997) *J. Biolog. Chem.* 272:19518–19524; Hromas, et al. (1997) *J. Immunol.* 159:2554–2558; Hedrick, et al. (1997) *J. Immunol.* 159:1589–1593; Gunn, etal. (1998) *Proc. Natl. Acad. Sci.* 95:258–263). CKβ-9 also induces both adhesion of lymphocytes to intercellular adhesion molecule-1 arrest of rolling cells (Campbell, et al. (1998) *Science* 279:381–384). All of the above properties are consistent with a role for CKβ-9 in regulating trafficking of lymphocytes through lymphoid tissues. CKβ-9 also inhibits hematopoietic progenitor colony formation (Hromas, et al., supra). Until the Applicants' discovery, no receptor for CKβ-9 was known. Both the amino acid and nucleic acid sequences of human CKβ-9 have been previously disclosed in PCT WO 96/25497, published on Aug. 22, 1996 and in PCT WO 96/06169, published on Feb. 29, 1996. CCR7 (also known as EBI1 and BLR2) (Birkenbach, etal (1993) *J. Virol.* 67: 2209–2220; Burgstahler, etal. (1995) *Biochem. Biophys. Res. Commun.* 215: 737–743) was previously known to be a receptor with only a single ligand, chemokine CKβ-11 (also known as ELC and MIP-3β) (Yoshie, et al. (1997) *J. Leukocyte Biol.* 62: 634–644; Yoshida, et al. (1997) *J. Biolog. Chem.* 272: 13803–13809). Both the amino acid and nucleic acid sequences of human CCR7 have been previously disclosed in PCT WO 94/12519, published on Jun. 9, 1994 and in PCT WO 94/12635, published on Jun. 9, 1994. In addition, both the amino acid and nucleic acid sequences of CKβ-11 have been previously disclosed in U.S. Pat. No. 5,605,817.

SUMMARY OF THE INVENTION

In one aspect, the present invention provides a method for the treatment of a subject in need of enhanced human CCR7 or CKβ-9 activity, said method comprising administering to the subject a therapeutically effective amount of an agonist and/or antagonist to said receptor.

Another aspect of the present invention provides methods of screening for compounds which bind to and activate (agonist) or inhibit activation (antagonist) of human CCR7 polypeptides (receptors) and/or their ligands, human CKβ-9 polypeptides, and interactions thereof.

In particular, the preferred method for identifying an agonist or antagonist comprises the steps of:

(a) in the presence of labeled or unlabeled ligand, contacting a cell expressing on the surface thereof a human CCR7 polypeptide (preferably that of SEQ ID NO: 1), said human CCR7 polypeptide being associated with a second component capable of providing a detectable signal in response to the binding of said ligand, with a compound to be screened under conditions to permit binding to the human CCR7 polypeptide; and (b) determining whether the compound binds to and activates or inhibits the human CCR7 polypeptide by measuring the level of a signal generated from the interaction of the compound with the CCR7 polypeptide.

In a further preferred embodiment, the method further comprises conducting the identification of agonist or antagonist in the presence of a ligand, wherein the ligand is labeled or unlabeled human CKβ-9 (preferably that of SEQ ID NO: 2).

In another embodiment, the method for identifying agonist or antagonist comprises the steps of:

(a) determining the inhibition of binding of a ligand to cells expressing on the surface thereof the CCR7 polypeptide (preferably that of SEQ ID NO: 1), or to cell membranes containing the polypeptide, in the presence of a candidate compound under conditions to permit binding to the polypeptide; and (b) determining the amount of ligand bound to the polypeptide, such that a compound capable of causing reduction of binding of a ligand is an agonist or antagonist.

Preferably, the ligand used in the above method is labeled or unlabeled human CKβ-9 polypeptide (preferably that of SEQ ID NO: 2).

Furthermore, the present invention relates to treating conditions associated with human CCR7 and/or CKβ-9 imbalance with the identified compounds.

Another object of the invention is to provide an antibody against the interaction of a human CCR7 receptor and a human CKβ-9 ligand

BRIEF DESCRIPTION OF THE DRAWINGS

FIG. 1 shows the deduced amino acid sequence of human CCR7 (also known as EBI1 or BLR2) receptor (SEQ ID NO: 1).

FIG. 2 shows the deduced amino acid sequence of human CKβ-9 (also known as SLC, 6Ckine, and exodus-2) (SEQ ID NO: 2).

DESCRIPTION OF THE INVENTION

Definitions

Figure 3:
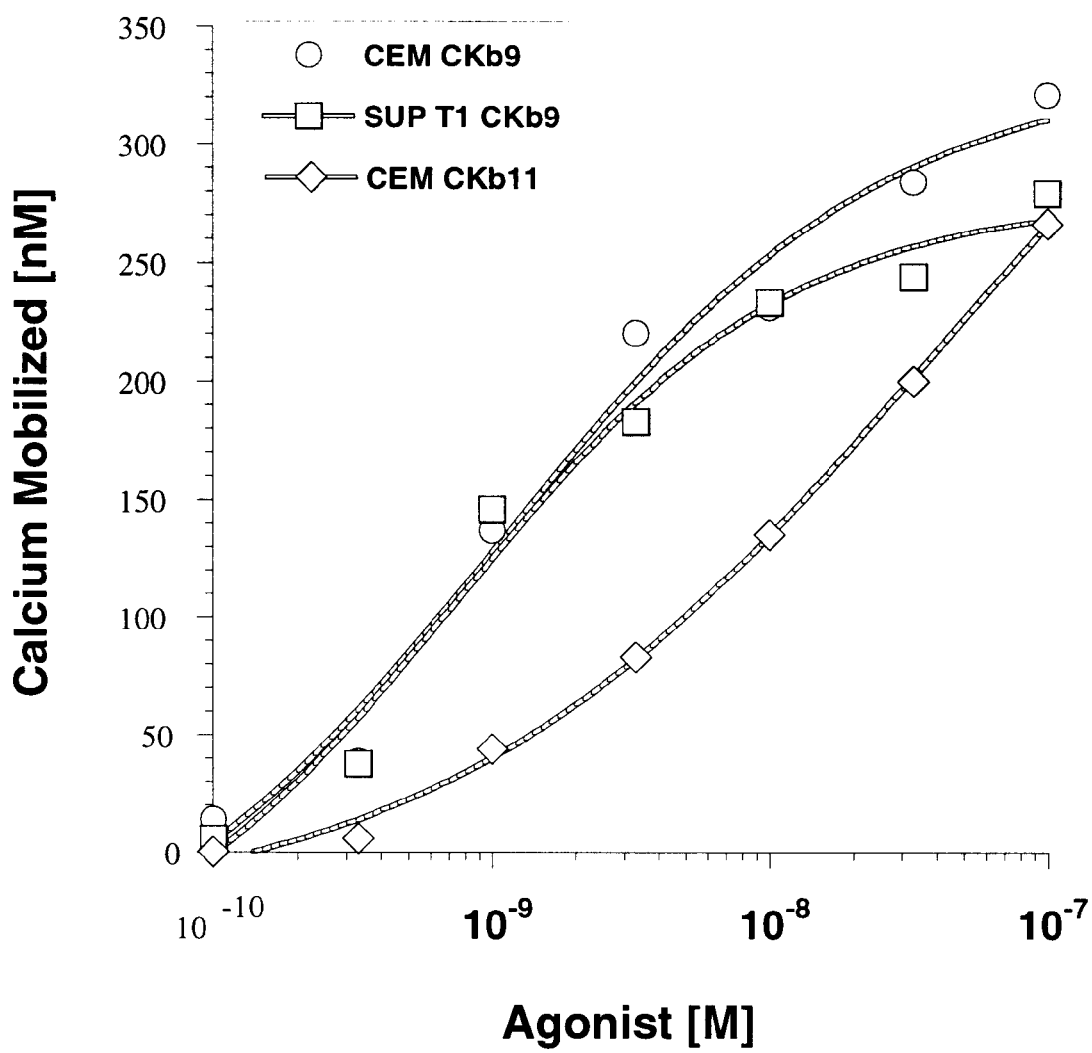
FIG. 3 shows CKb-9 concentration-response-curves in two T-cell lines, CEM and Sup-T1. Also shown is the CKb-11 concentration-response-curve in CEM cells using the single cuvette calcium assay.
Figure 4:
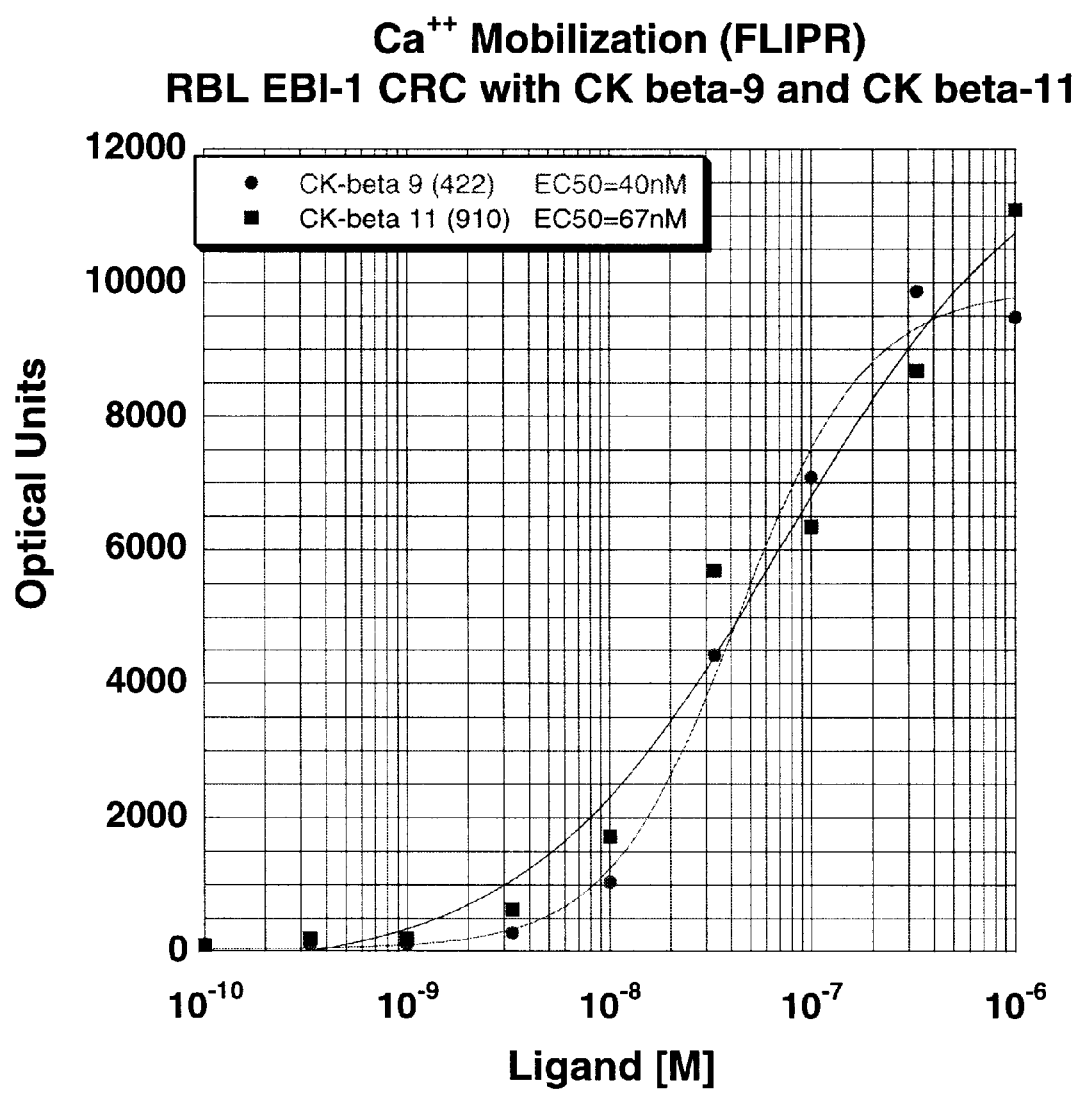
FIG. 4 shows the concentration-response-curve for CKb-9 and CKb-11 in RBL-2H3-CCR7 cells using the FLIPR technology.
Figure 5:
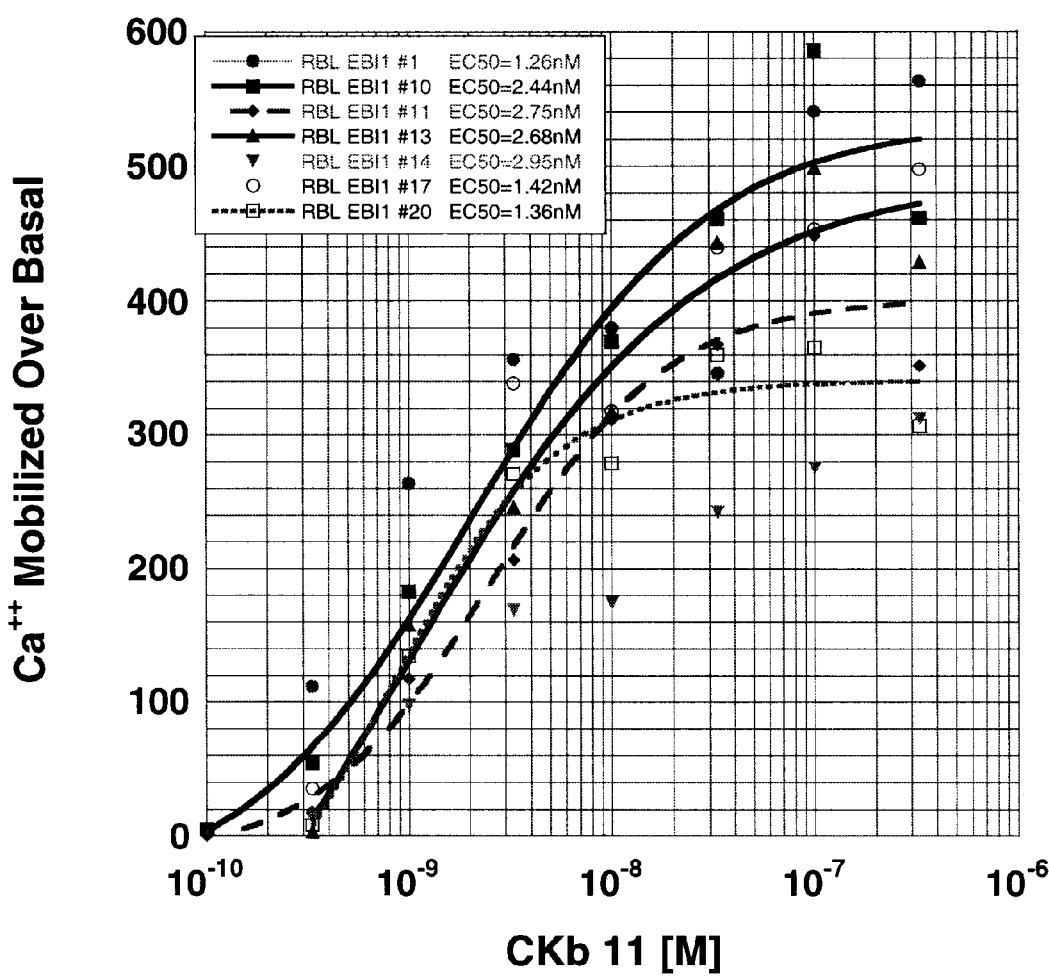
FIG. 5 shows the concentration-response-curves for CKb-11 evaluating seven message positive RBL-2H3-CCR7 receptor clones using the single cuvette calcium assay.
Figure 6:
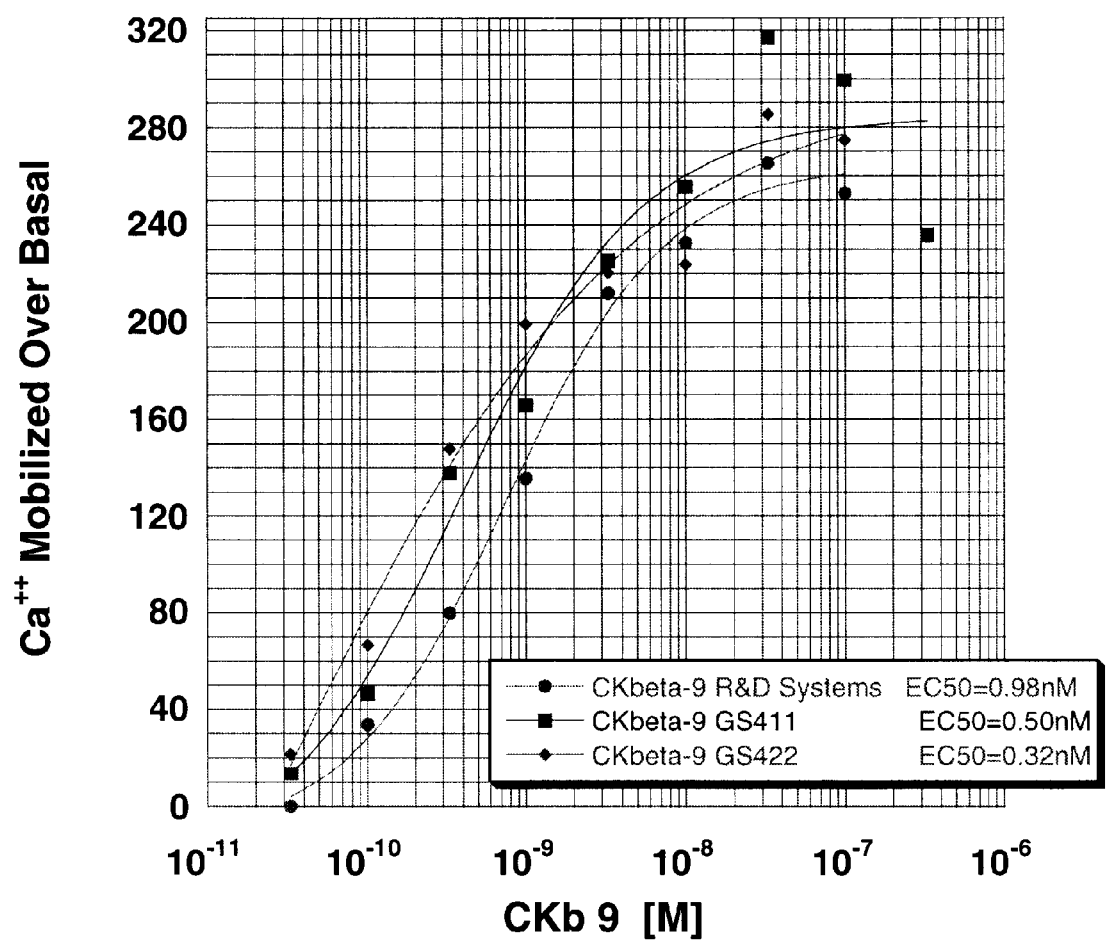
FIG. 6 shows a comparison of the potency of three forms of CKb-9 in RBL-2H3-CCR7 cells using the single cuvette calcium assay.

The following definitions are provided to facilitate understanding of certain terms used frequently herein.

"Human CCR7" or "Human CCR7 polypeptides" or "Human CCR7 receptors" refer generally to polypeptides having the amino acid sequence with at least 80% identity with the amino acid as set forth in SEQ ID NO: 1, including allelic variants of SEQ ID NO: 1. Preferably, "Human CCR7" or "Human CCR7 polypeptides" or "Human CCR7 receptors" is polypeptide with the amino acid sequence of SEQ ID NO: 1. "Human CKβ-9" or "Human CKβ-9 polypeptides" or "Human CKβ-9 ligands" refer generally to polypeptides having the amino acid sequence with at least 80% identity with the amino acid as set forth in SEQ ID NO: 2, including allelic variants of SEQ ID NO: 1. Preferably, "Human CK,-9" or "Human CKβ-9 polypeptides" or "Human CKβ-9 ligands" is polypeptide with the amino acid sequence of SEQ ID NO: 2.

"Receptor Activity" or "Biological Activity of the Receptor" refers to the metabolic or physiologic function of said human CCR7 including similar activities or improved activities or these activities with decreased undesirable side-effects. Also included are antigenic and immunogenic activities of said human CCR7.

"Human CCR7 gene" or "Human CCR7 polynucleotide" refer to a polynucleotides containing a nucleotide sequence which encodes a human CCR7 polypeptide.

"Human CKβ-9 gene" or "Human CKβ-9 polynucleotide" refer to a polynucleotides containing a nucleotide sequence which encodes a human CCR7 polypeptide.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS-STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990)182:626–646 and Rattan, et al., "Protein Synthesis: Posttranslational Modifications and Aging", *Ann. NY Acad. Sci.* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Altschul, S. F., et al., *J. Molec. Biol.* 215: 403–410 (1990). The BLAST X program is publicly available from NCBI and other sources (BLAST Manual, Altschul, S., et at., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, *J. Mol Biol.* 48: 443–453 (1970) Comparison matrix: BLOSSUM62 from Hentikoff and Hentikoff, 89:10915–10919 (1992) *Proc. Natl. Acacd. Sci. USA.*

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, *J. Mol Biol.* 48: 443–453 (1970)

Comparison matrix: matches =+10, mismatch =0

Gap Penalty: 50

Gap Length Penalty: 3

Available as: The "gap" program from Genetics Computer Group, Madison Wis. These are the default parameters for nucleic acid comparisons.

Preferred polynucleotide embodiments further include an isolated polynucleotide comprising a polynucleotide sequence having at least a 50, 60, 70, 80, 85, 90, 95, 97 or 100% identity to the polynucleotide sequence that encodes SEQ ID NO: 1, wherein said polynucleotide sequence may be identical to a polynucleotide sequence encoding SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in a polynucleotide sequence encoding SEQ ID NO: 1 by the integer defining the percent identity divided by 100 and then subtracting that product from said total number of nucleotides encoding SEQ ID NO: 1, or:

$$n_n\ x_n-(x_n\ y),$$

wherein $n_n$ is the number of nucleotide alterations, $x_n$ is the total number of nucleotides in the polynucleotide sequence encoding SEQ ID NO: 1, y is 0.50 for 50%, 0.60 for 60%, 0.70 for 70%, 0.80 for 80%, 0.85 for 85%, 0.90 for 90%, 0.95 for 95%, 0.97 for 97% or 100%, and is the symbol for the multiplication operator, and wherein any non-integer product of $x_n$ and y is rounded down to the nearest integer prior to subtracting it from $x_n$. Alterations of a polynucleotide sequence encoding SEQ ID NO: 1 may create nonsense, missense or frameshift mutations in this coding sequence and thereby alter the polypeptide encoded by the polynucleotide following such alterations.

By way of example, a polynucleotide sequence of the present invention may be identical to a polynucleotide sequence encoding SEQ ID NO: 1, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO: 1 by the integer defining the percent identity divided by 100 and then subtracting that product from said total number of amino acids in SEQ ID NO: 1, or:

$$n_n=x_n-(x_n\ y),$$

wherein $n_n$ is the number of amino acid alterations, $x_n$ is the total number of amino acids in SEQ ID NO: 1, y is, for instance 0.70 for 70%, 0.80 for 80%, 0.85 for 85% etc., is the symbol for the multiplication operator, and wherein any non-integer product of $x_n$ and y is rounded down to the nearest integer prior to subtracting it from $x_n$.

Preferred polypeptide embodiments further include an isolated polypeptide comprising a polypeptide having at least a 50, 60, 70, 80, 85, 90, 95, 97 or 100% identity to the polypeptide sequence of SEQ ID NO: 1, wherein said polypeptide sequence may be identical to the reference sequence of SEQ ID NO: 1 or may include up to a certain integer number of amino acid alterations as compared to SEQ ID NO: 1, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 1 by the integer defining the percent identity divided by 100 and then subtracting that product from said total number of amino acids in SEQ ID NO: 1, or:

$$n_a\ x_a-(x_a\ y),$$

wherein $n_a$ is the number of amino acid alterations, $x_a$ is the total number of amino acids in SEQ ID NO: 1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to SEQ ID NO: 1, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino-or carboxy-terminal positions of the reference polypeptide sequence or anywhere between those teirninal positions, interspersed either individually among the amino acids in the reference sequence or in one or more contiguous groups within the reference sequence. The number of amino acid alterations for a given % identity is determined by multiplying the total number of amino acids in SEQ ID NO: 1 by the integer defining the percent identity divided by 100 and then subtracting that product from said total number of amino acids in SEQ ID NO: 1, or:

$$n_a=x_a-(x_a\ y),$$

wherein $n_a$ is the number of amino acid alterations, $x_a$ is the total number of amino acids in SEQ ID NO: 1, y is, for instance 0.70 for 70%, 0.80 for 80%, 0.85 for 85% etc., and is the symbol for the multiplication operator, and wherein any non-integer product of $x_a$ and y is rounded down to the nearest integer prior to subtracting it from $x_a$.

Polypeptides of the Invention

The human CCR7 polypeptides of the present invention include the polypeptide of SEQ ID NO: 1 as well as polypeptides which have at least 80% identity to the polypeptide of SEQ ID NO: 1, or the relevant portion, and more preferably at least 85% identity, and still more preferably at least 90% identity, and even still more preferably at least 95% identity to SEQ ID NO: 1. The human CKβ-9 polypeptides of the present invention include the polypeptide of SEQ ID NO: 2 (in particular the mature polypeptide) as well as polypeptides which have at least 80% identity to the polypeptide of SEQ ID NO: 2 or the relevant portion and more preferably at least 85% identity, and still more preferably at least 90% identity, and even still more preferably at least 95% identity to SEQ ID NO: 2.

Preferably, all of these polypeptides retain the biological activity of the receptor, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The human CCR7 and CKβ-9 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides, Vectors, Host Cells, Expression

Another aspect of the invention relates to isolated polynucleotides which encode the human CCR7 and CKβ-9 polypeptides. The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis, et al., BASIC METHODS IN MOLECULAR BIOLOGY (1986) and Sambrook, et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, RBL-2H3, K562, HeLa, C127, 3T3, BHK, 293 and Bowes melanoma cells; and plant cells.

A great variety of expression systems can be used. Such systems include, among others, chromosomal, episomal and virus-derived systems, vectors derived from bacterial plasmids, from bacteriophage, from transposons, from, e.g., yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook, et al., MOLECULAR CLONING, A LABORATORY MANUAL (supra). For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the human CCR7 polypeptide is to be expressed for use in screening assays, generally, it is preferred that the polypeptide be produced at the surface of the cell. In this event, the cells may be harvested prior to use in the screening assay. If human CCR7 polypeptide is secreted into the medium, the medium can be recovered in order to recover and purify the polypeptide; if produced intracellularly, the cells must first be lysed before the polypeptide is recovered.

Human CCR7 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well-known techniques for refolding proteins may be employed to regenerate active conformation when the polypeptide is denatured during isolation and or purification.

Antibodies

The polypeptides of the invention or their fragments or analogs thereof, or cells expressing them can also be used as immunogens to produce antibodies immunospecific for the human CCR7 and/or CKβ-9 polypeptides. The term "immunospecific" means that the antibodies have substantially greater affinity for the polypeptides of the invention than their affinity for other related polypeptides in the prior art.

Antibodies generated against the human CCR7 and/or CKβ-9 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, et al., *Nature* (1975) 256:495–497), the trioma technique, the human B-cell hybridoma technique (Kozbor, et al., *Immunology Today* (1983) 4:72) and the EBV-hybridoma technique (Cole, et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography. In addition, antibodies against a human CKβ-9 ligand may be employed to inhibit interaction of such a ligand with the human CCR7 receptor and may be useful in the treatment of diseases or disorders, including, but not limited to: allergic disorders, autoimmune diseases, ischemia/reperfusion injury, development of atherosclerotic plaques, cancer (including mobilization of hematopoietic stem cells for use in chemotherapy or myeloprotection during chemotherapy), chronic inflammatory disorders, chronic rejection of transplanted organs or tissue grafts, chronic myelogenous leukemia, and infection by HIV and other pathogens.

Screening Assays

A human CCR7 receptor polypeptide may be employed in a process for screening for compounds which bind the receptor and which activate (called agonists) or inhibit the activation of (called antagonists) the human CCR7 polypeptide receptor.

Thus, human CCR7 polypeptides may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan, et al., *Current Protocols in Immunology* 1(2):Chapter 5 (1991).

Human CCR7 proteins are responsible for many biological functions, including many pathologies. Provided by the invention are screening methods to identify compounds that stimulate or that inhibit the function the function or level of the polypeptide. In general, agonists are employed for therapeutic and prophylactic purposes for such conditions as: allergic disorders, autoimmune diseases, ischemia/reperfusion injury, development of atherosclerotic plaques, cancer (including mobilization of hematopoietic stem cells for use in chemotherapy or myeloprotection during chemotherapy), chronic rejection of transplanted organs or tissue grafts, chronic myelogenous leukemia, and infection by HIV and other pathogens.

In general, such screening procedures involve providing appropriate cells that express the human CCR7 polypeptide receptor on the surface thereof. Such cells include cells from mammals, yeast, Drosophila or *E. coli*. In particular, a polynucleotide encoding the receptor of the present invention is employed to transfect cells to thereby express the human CCR7 polypeptide receptor. The expressed receptor is then contacted with a test compound to observe binding, stimulation or inhibition of a functional response.

One such screening procedure involves the use of melanophores that are transfected to express the human CCR7 polypeptide receptor. Such a screening technique is described in PCT WO 92/01810, published Feb. 6, 1992. Such an assay may be employed to screen for a compound which inhibits activation of the human CCR7 receptor polypeptide by contacting the melanophore cells encoding the receptor with both the receptor ligand, such as CKβ-9 polypeptide (SEQ ID NO: 2), and a compound to be screened. Inhibition of the signal generated by the ligand indicates that a compound is a potential antagonist for the receptor, i.e., inhibits activation of the receptor.

The technique may also be employed for screening of compounds that activate the receptor by contacting such cells with compounds to be screened and determining whether such a compound generates a signal, i.e., activates the receptor.

Other screening techniques include the use of cells that express the human CCR7 receptor polypeptide (for example, transfected CHO cells) in a system which measures extracellular pH changes caused by receptor activation. In this technique, compounds may be contacted with cells expressing the receptor polypeptide. A second messenger response, e.g., signal transduction or pH changes, is then measured to determine whether the potential compound activates or inhibits the receptor.

Another screening technique involves expressing the human CCR7 polypeptide receptor in cells in which the receptor is linked to phospholipase C or D. Representative examples of such cells include, but are not limited to: endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds that are antagonists, and thus inhibit activation of the human CCR7 polypeptide receptor by determining inhibition of binding of labeled ligand, such as CKβ-9, to cells which have the receptor on the surface thereof, or cell membranes containing the receptor. Such a method involves transfecting a eukaryotic cell with DNA encoding the human CCR7 polypeptide receptor such that the cell expresses the receptor on its surface. The cell is then contacted with a potential antagonist in the presence of a labeled form of a ligand, such as CKβ-9. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay. Naturally, this same technique can be used to look for an agonist.

Another screening procedure involves the use of mammalian cells (CHO, HEK 293, Xenopits Oocytes, RBL-2H3, etc.) that are transfected to express the receptor of interest. The cells are loaded with an indicator dye that produces a fluorescent signal when bound to calcium, and the cells are contacted with a test substance and a receptor agonist, such as CKβ-9. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, Xenopties Oocytes, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as CKβ-9, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another screening technique for antagonists or agonists involves introducing RNA encoding the human CCR7 polypeptide receptor into Xetiopits oocytes (or CHO, HEK 293, RBL-2H3, etc.) to transiently or stably express the receptor. The receptor oocytes are then contacted with the receptor ligand, such as CKβ3–9, and a compound to be screened. Inhibition or activation of the receptor is then determined by detection of a signal, such as, cAMP, calcium, proton, or other ions.

Another method involves screening for human CCR7 polypeptide receptor inhibitors by determining inhibition or stimulation of human CCR7 polypeptide receptor-mediated cAMP and/or adenylate cyclase accumulation or dimunition. Such a method involves transiently or stably transfecting a eukaryotic cell with human CCR7 polypeptide receptor to express the receptor on the cell surface. The cell is then exposed to potential antagonists in the presence of human CCR7 polypeptide receptor ligand, such as CKβ-9. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits human CCR7 receptor polypeptide-ligand binding, the levels of human CCR7 polypeptide receptor-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating-type cells which triggers a MAP kinase cascade leading to G1 arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, et al., *Nature* 384: 14–16, 1996; Manfredi, et al., *Mol. Cell. Biol.* 16: 4700–4709, 1996). This provides a rapid direct growth selection (e.g., using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUS1-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for identifying new ligands not known to be capable of binding to human CCR7 polypeptide receptors. The screening assays described above for identifying agonists may be used to identify new ligands.

The present invention also contemplates agonists and antagonists obtainable from the above described screening methods.

Examples of potential human CCR7 polypeptide receptor antagonists include peptidomimetics, synthetic organic molecules, natural products, antibodies, etc., which bind to the receptor, but do not elicit a second messenger response, such that the activity of the receptor is prevented.

Potential antagonists also include proteins which are closely related to the ligand of the human CCR7 polypeptide receptor, i.e., a fragment of the ligand, which have lost biological function, and when they bind to the human CCR7 polypeptide receptor, elicit no response.

Thus in another aspect, the present invention relates to a screening kit for identifying agonists, antagonists, and ligands for the human CCR7 polypeptide receptor, which comprises:

(a) a human CCR7 polypeptide receptor, preferably that of SEQ ID NO: 1; and further preferably comprises labeled or unlabeled CKβ3–9, preferably that of SEQ ID NO: 2;

(b) a recombinant cell expressing a human CCR7 polypeptide receptor, preferably that of SEQ ID NO: 1; and further preferably comprises labeled or unlabeled CKβ-9, preferably that of SEQ ID NO: 2; or (c) a cell membrane expressing human CCR7 polypeptide receptor; preferably that of SEQ ID NO: 1; and further preferably comprises labeled or unlabeled CKβ-9, preferably that of SEQ ID NO: 2.

It will be appreciated that in any such kit, (a), (b), or (c) may comprise a substantial component.

As noted above, a potential antagonist is a small molecule that binds to the human CCR7 polypeptide receptor, making it inaccessible to ligands such that normal biological activity is prevented. Examples of small molecules include, but are not limited to, small peptides or peptide-like molecules.

Potential antagonists also include soluble forms of the human CCR7 polypeptide receptor, e.g., fragments of the receptor, which bind to the ligand and prevent the ligand from interactinig with membrane bound human CCR7 polypeptide receptors.

Potential antagonists also include soluble forms of a human CCR7 polypeptide, e.g., fragments of the polypeptide, which bind to the ligand and prevent the ligand from interacting with membrane bound human CCR7 polypeptides. Potential antagonists also include antibodies that bind to the CKβ-9 ligand and prevent the ligand from binding or activating the human CCR7 receptor. Human CCR7 proteins are found in multiple classes of lymphocytes in the mammalian host and are responsible for many biological functions, including many pathologies. Accordingly, it is desirous to find compounds and drugs that stimulate or inhibit the function of human CCR7. The biological functions of CKβ-9 and CCR7 in healthy humans and in diseases is unknown. The observed expression of messenger RNA's for this ligand and receptor in immune tissues such as lymph nodes, and the activity of CKβ-9 in promoting chemotaxis of T cells carrying CCR7, suggest that CKβ-9/CCR7 interactions may promote immune system responses to foreign antigens. Antagonists may, therefore, be of use in treating or preventing allergic and autoimmune diseases, chronic inflammatory disorders, and tissue and organ graft rejection. CKβ-9 expression has also been detected by RT-pcr in atherosclerotic plaques, suggesting that CKβ-9 might promote plaque formation. Antagonists might, therefore, also be of use in treating or preventing atherosclerosis, ischemia/reperfusion injury, and infection by HIV, and other pathogens. In general, CKβ-9 agonists are employed for therapeutic and prophylactic purposes for such conditions as infections, hematological disorders such as chronic myelogenous leukemia, use as myeloprotectants which reduce cell death during chemotherapy, or as stem cell mobilizers which can be used to obtain stem cells that can be administered to a chemotherapy patient to restore cells killed by chemotherapy.

Figure 7:
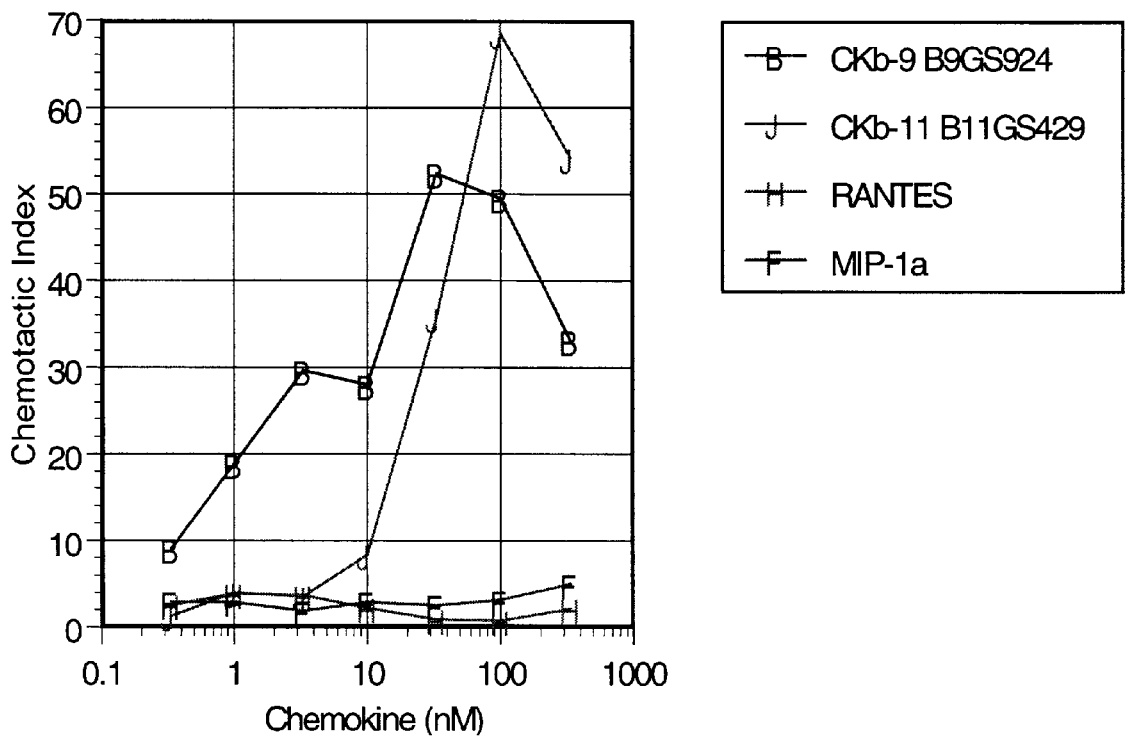
FIG. 7 shows chemotaxis of Sup-T1 cells in response to various chemokines.

Sup-T1 cells, a human immature leukemia T cell line, are described in Hecht, F. (1984) *Science* 226:1445–1447 and are available from the American Type Culture Collection, ATCC accession # CRL- 1942. Example 2 shows that Sup-T1 cells carry RNA encoding the human CCR7 receptor. Moreover, Example 1 and FIGS. 3 and 7 show calcium mobilization and chemotaxis in response to stimulation with CKβ-9. Therefore, the Applicants herein disclose that Sup-T1 cells can be used to screen for agonists and antagonists of the interaction between human CKβ-9 ligand and human CCR7 receptor.

CEM cells are a human lymphoblastic leukemia T-cell line and are available from the American Type Culture Collection, ATCC accession # ACC-145. Example 1 and FIG. 3 show that CEM cells show calcium mobilization and chemotaxis when induced with either CKβ-9 or CK-11. These data suggest that CEM cells carry human CCR7 receptor. Therefore, the Applicants herein disclose that CEM cells can be used to screen for agonists and antagonists of the interaction between human CKβ-9 and human CCR7 receptor. Furthermore, the Applicants claim the use of other cell lines which also carry the RNA for CCR7 and, therefore, may be used for identifying agonists and antagonists of the interaction between human CKβ-9 and human CCR7 receptor in one of the screening techniques discussed above.

Although the types of screening methods herein disclosed, which could be used with either Sup-T1 cells or CEM cells, are well known in that art, such screens preferably employ radioligand binding assays, calcium mobilization assays, intracellular or receptor protein phosphorylation or chemotaxis of the cells.

Prophylactic and Therapeutic Methods

This invention provides methods of treating an abnormal conditions related to both an excess of and insufficient amounts of human CCR7 receptor and/or human CKβ-9 ligand activity.

If the activity of human CCR7 receptor and/or human CKβ-9 ligand is in excess, several approaches are available. One approach comprises administering to a subject an inhibitor compound (antagonist) as hereinabove described along with a pharmaceutically acceptable carrier in an amount effective to inhibit activation by blocking binding of human CKβ-9 ligand to the human CCR7 receptor, or by inhibiting a second signal, and thereby alleviating the abnormal condition.

In another approach, soluble forms of human CCR7 polypeptides still capable of binding the ligand in competition with endogenous human CCR7 may be administered. Typical embodiments of such competitors comprise fragments of the human CCR7 polypeptide.

For treating abnormal conditions related to an underexpression of human CCR7 receptor and its activity and/or human CKβ-9 ligand and its activity, several approaches are also available. One approach comprises administering to a subject a therapeutically effective amount of a compound which activates human CCR7, i.e., an agonist as described above, in combination with a pharmaceutically acceptable carrier, to thereby alleviate the abnormal condition.

Formulation and Administration

Agonists and antagonists discovered by the methods described herein may be formulated in combination with a suitable pharmaceutical carrier. Such formulations comprise a therapeutically effective amount of the agonists or antagonist, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Agonists or antagonists of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

EXAMPLES

BIOLOGICAL METHODS

Example 1

Calcium Mobilization and Desensitization Assays with CKβ-9 and RBL-2H3 Cells Carrying CCR7:

(a): Bioassays:

The functional activity of an antagonist of the CKβ-9/CCR7 receptor is demonstrated using the CKβ-9-induced $Ca^{2+}$ mobilization in RBL-2H3 cells stably expressing CCR7 (RBL-2H3-CCR7).

(b): RBL-2H3-CCR7 Cell Culture Conditions:

RBL-2H3-CCR7 cells were cultured to near confluence in T-150 flasks at 37° C. in a humidified incubator with 5%

$CO_2$/95% air in Earls MEM with Earls salts (Gibco) supplemented with non-essential amino acids and L-glutamate, with 10% fetal calf serum (Gibco) and 400 µg/ml G418 (Gibco).

c: Fluorescent Measurements-Calcium Mobilization:

The functional assay used to assess antagonist activity of compounds was CKβ-9-induced calcium mobilization in intact RBL-2H3-CCR7 cells. Cells were washed with 50 mM Tris, pH 7.4 containing 1 mM EDTA. The $[Ca^{2+}]_i$ was estimated with the calcium fluorescent probe fura 2 (Grynkiewicz, et al., J. Biol. Chem., 1985, 260, 3440–3450). The media was aspirated from RBL-2H3-CCR7 cells that were near confluence in T-150 flasks then 40 ml in Krebs Ringer Hensilet containing 0.1% BSA, 1.1 mM $MgCl_2$ and 5 mM HEPES, pH 7.4 (buffer A) was added. The diacetoxymethoxy ester of fura 2 (fura 2/AM) was added at a concentration of 2 µM and incubated for 45 min at 37° C. Buffer A was aspirated off the RBL-2H3-CCR7 cells and 40 ml of Buffer A was added to the cells and incubated for an additional 20 min to allow complete hydrolysis of the entrapped ester. Buffer A was aspirated and cells covered with ~5ml of Delbeccos Phosphate Buffered Saline with 1 mM EDTA (no calcium or magnesium) for 5 min at 37° C. Buffer is aspirated off and 40 ml of buffer A added to the cells which were then mechanically detached from the flasks. Cells were maintained at room temperature until used in the fluorescent assay which was performed within 3 hours.

The fluorescence of fura 2 containing cells was measured with a fluorometer designed by the Johnson Foundation Biomedical Instrumentation Group. The fluorometer was equipped with a temperature control and a magnetic stirrer under the cuvette holder. Wavelengths were set at 340 nm (10 nm band width) for excitation and 510 nm (20 nm band width) for emission. All experiments were performed at 37° C. with constant stirring. For compound studies, fura 2 loaded cells were centrifuged and resuspended in buffer A containing 1 mM $CaCI_2$ minus BSA at $10^6$ cells/mL. For assessment of agonist activity, a 2 mL aliquot of RBL-2H3-CCR7 cells was added to a cuvette and warmed in a water bath to 37° C. The 1 $cm^2$ cuvette was transferred to the fluorometer and fluorescence was recorded for 15 seconds to ensure a stable baseline before addition of compound. Fluorescence was recorded continuously for up to 2 mins after addition of compounds to monitor for the presence of any agonist activity.

For antagonist studies, varying concentrations of compounds or vehicle were added to the fura 2 loaded RBL-2H3-CCR7 cells and monitored for 1 min to ensure that there was no change in baseline fluorescence followed by the addition of 10 nM CKβ9. The maximal $[Ca^{2+}]$/fura 2 fluorescence was then determined for each sample. The $[Ca^{2+}]_i$ was calculated using the following formula:

$$[Ca^{2+}]_i = 224 (nM) \frac{F - F_{min}}{F_{max} - F}$$

The percent of maximal CKβ9 (10 nM) induced $[Ca^{2+}]_i$ was determined for each concentration of compound and the $IC_{50}$ defined as the concentration of test compound that inhibits 50% of the maximal CKβ9 response. Concentration response curves (5–7 concentrations) were run.

(d) High-Throughput-Screening-Calcium Assay:

The calcium assay described above was converted to a high-throughput-screen (HTS) with the use of a 96 well Fluorescent Imaging Plate Reader (FLIPR) from Biomolecular Devices. This technology allows the measurement of the intracellular calcium mobilization in cells attached to the bottom of a 96 well plate. For this procedure, cells were obtained from the T-150 flasks as described above. The cells were plated into the 96 well plate at 30,000 cells/well. With incubation in a humidified environment in a cell incubator at 37° C. for 18–24 hours, the cells attached to the bottom surface of the 96 well plate.

The FLIPR works best with the visible wavelength calcium indicators, Fluo-3 and Calcium green-1. Both of these dyes have been used successfully for the HTS assay, but Fluo-3 was generally used. Typically 4 µM Fluo-3 was loaded into the cells for 1 hr at 37° C. in cell media without fetal calf serum and with 1.5 mM sulfinpyrazone to inhibit dye release from the cells. The media is aspirated from the cells and fresh media was added for 10 min at 37° C. to allow hydrolysis of the dye and remove extracellular dye. The media was aspirated and replaced with KRH buffer (buffer A above). After 10 min at 37° C. the cells were placed in FLIPR apparatus for analysis.

FLIPR has 3–96 well plates. In addition to the plate with dye loaded cells, there is a plate containing varying concentrations of compound or vehicle and the third plate has the agonist at varying concentrations to establish agonist potency or a single concentration, e.g., 10 nM of CKβ9 for antagonist activity. For antagonist studies, FLIPR obtains a baseline fluorescence for ~30 sec, then it adds the compounds to all 96 wells simultaneously and begins to monitor changes in intracellular $Ca^{2+}$. After 2 min, the contents or the agonist plate is added to the cells. The inhibition of the CKβ9 response in the presence of vehicle for the various concentrations of compound is determined essentially as described for the single cuvette Fura-2 assay described above.

Example 2

Evidence of CCR7 in Sup-T1 Cells:

RNA was purified from Sup-T1 cells. Sequences related to chemokine receptors were identified in this RNA using a procedure known as 3'-RACE (Rapid Amplification of cDNA Ends). The procedure was carried out using a kit from Life Technologies, Rockville Md., known as the "3'-RACE System". In this system, the RNA was transcribed into cDNA using primer AP (supplied with the kit). Chemokine receptor-related DNA sequences were then generated from the cDNA using two rounds of PCR employing degenerate primers that contain sequences that are conserved (but not identical) among many known chemokine receptors. The first round of PCR (30 cycles) used primer UAP (supplied with the kit) and degenerate primer 5'-GGGAATTCCAACCTGGCC(A/T)T(T/G)(T/G)C(T/G) GACCT (SEQ ID NO: 3). The second round of PCR (30 cycles) employed the above degenerate primer in combination with degnerate primer 5'-GCCCTCGAGGAC(G/A)AT (G/A)GCCAGGTA(C/T/A)C(T/G)(G/A)TC (SEQ ID NO: 4). The products of these PCR reactions were cloned and sequenced. One of these PCR products was identical in DNA sequence (over 183 nucleotides sequenced) to the published sequence of CCR7 in PCT WO 94/12519, published on Jun. 9, 1994 and in PCT WO 94/12635, published on June 9.

Example 3

Ligand Bank for Binding and Functional Assays:

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e., calcium, cAMP, microphysiometer, oocyte electrophysiology, etc., see below) as well as binding assays.

Example 4
Ligand Binding Assays:

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xelopits oocytes in response to agonist exposure. Recordings are made in Ca2+ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is identified.

Example 8
Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method for identifying an agonist or antagonist of the interaction between a human CC Chemokine Receptor 7 (CCR7) polypeptide and a human Chemokine Beta-9 (CKβ-9) polypeptide, wherein the CCR7 polypeptide has an amino acid sequence comprising SEQ ID NO: 1 and the CKβ-9 polypeptide has an amino acid sequence comprising SEQ ID NO: 2, said method comprising:

(a) in the presence of labeled or unlabeled said human CKβ-9 polypeptide, contacting a cell expressing on the surface thereof said human CCR7 polypeptide, said human CCR7 polypeptide being associated with a second component capable of providing a detectable signal in response to the binding of said human CKβ-9 polypeptide to said human CCR7 polypeptide, with a compound; and (b) determining whether the compound activates or inhibits said detectable signal, wherein a compound that activates said signal is an agonist and a compound that inhibits said signal is an antagonist.

2. A method for identifying agonists and antagonists of the interaction between a human CC Chemolkine Receptor 7 (CCR7) polypeptide and a human Chemokine Beta-9 (CKβ-9) polypeptide, wherein the CCR7 polypeptide has an amino acid sequence comprising SEQ ID NO: 1 and the CKβ-9 polypeptide has an amino acid sequence comprising SEQ ID NO: 2, said method comprising:

(a) in the presence of labeled or unlabeled said human CKβ-9 polypeptide, contacting a cell expressing on the surface thereof said human CCR7 polypeptide, with a compound; and (b) determining whether the compound causes a reduction in the binding of said human CKβ-9 polypeptide to said human CCR7 polypeptide, wherein a compound that causes a reduction in said binding is either an agonist or antagonist.

3. The method as claimed in claim 1, wherein the cell is selected from the group consisting of: a Sup-T1 cell, a CEM cell, and a RBL-2H3 cell, wherein each cell type is transfected with a vector enabling expression of said CCR7 polypeptide.

4. The method as claimed in claim 2, wherein the cell is selected from the group consisting of: a Sup-T1 cell, a CEM cell, and a RBL-2H3 cell, wherein each cell type is transfected with a vector enabling expression of said CCR7 polypeptide.

* * * * *

SEQUENCE LISTING

<160> NUMBER OF SEQ ID NOS: 2

<210> SEQ ID NO 1
<211> LENGTH: 378
<212> TYPE: PRT
<213> ORGANISM: Human

<400> SEQUENCE: 1

Met Asp Leu Gly Lys Pro Met Lys Ser Val Leu Val Val Ala Leu Leu

```
                1               5                   10                  15
            Val Ile Phe Gln Val Cys Leu Cys Gln Asp Glu Val Thr Asp Asp Tyr
                            20              25              30
            Ile Gly Asp Asn Thr Thr Val Asp Tyr Thr Leu Phe Glu Ser Leu Cys
                        35              40              45
            Ser Lys Lys Asp Val Arg Asn Phe Lys Ala Trp Phe Leu Pro Ile Met
            50              55                  60
            Tyr Ser Ile Ile Cys Phe Val Gly Leu Leu Gly Asn Gly Leu Val Val
            65                  70              75                      80
            Leu Thr Tyr Ile Tyr Phe Lys Arg Leu Lys Thr Met Thr Asp Thr Tyr
                            85              90                  95
            Leu Leu Asn Leu Ala Val Ala Asp Ile Leu Phe Leu Leu Thr Leu Pro
                        100             105             110
            Phe Trp Ala Tyr Ser Ala Ala Lys Ser Trp Val Phe Gly Val His Phe
                    115             120             125
            Cys Lys Leu Ile Phe Ala Ile Tyr Lys Met Ser Phe Phe Ser Gly Met
                130             135             140
            Leu Leu Leu Leu Cys Ile Ser Ile Asp Arg Tyr Val Ala Ile Val Gln
            145             150             155                     160
            Ala Val Ser Ala His Arg His Arg Ala Arg Val Leu Leu Ile Ser Lys
                            165             170             175
            Leu Ser Cys Val Gly Ile Trp Ile Leu Ala Thr Val Leu Ser Ile Pro
                        180             185             190
            Glu Leu Leu Tyr Ser Asp Leu Gln Arg Ser Ser Glu Gln Ala Met
                    195             200             205
            Arg Cys Ser Leu Ile Thr Glu His Val Glu Ala Phe Ile Thr Ile Gln
                210             215             220
            Val Ala Gln Met Val Ile Gly Phe Leu Val Pro Leu Leu Ala Met Ser
            225             230             235                     240
            Phe Cys Tyr Leu Val Ile Ile Arg Thr Leu Leu Gln Ala Arg Asn Phe
                            245             250             255
            Glu Arg Asn Lys Ala Ile Lys Val Ile Ile Ala Val Val Val Val Phe
                        260             265             270
            Ile Val Phe Gln Leu Pro Tyr Asn Gly Val Val Leu Ala Gln Thr Val
                    275             280             285
            Ala Asn Phe Asn Ile Thr Ser Ser Thr Cys Glu Leu Ser Lys Gln Leu
            290             295             300
            Asn Ile Ala Tyr Asp Val Thr Tyr Ser Leu Ala Cys Val Arg Cys Cys
            305                 310             315                 320
            Val Asn Pro Phe Leu Tyr Ala Phe Ile Gly Val Lys Phe Arg Asn Asp
                            325             330             335
            Leu Phe Lys Leu Phe Lys Asp Leu Gly Cys Leu Ser Gln Glu Gln Leu
                        340             345             350
            Arg Gln Trp Ser Ser Cys Arg His Ile Arg Arg Ser Ser Met Ser Val
                    355             360             365
            Glu Ala Glu Thr Thr Thr Thr Phe Ser Pro
                370                 375

<210> SEQ ID NO 2
<211> LENGTH: 134
<212> TYPE: PRT
<213> ORGANISM: Human

<400> SEQUENCE: 2
```

-continued

```
Met Ala Gln Ser Leu Ala Leu Ser Leu Leu Ile Leu Val Leu Ala Phe
 1               5                  10                  15

Gly Ile Pro Arg Thr Gln Gly Ser Asp Gly Gly Ala Gln Asp Cys Cys
             20                  25                  30

Leu Lys Tyr Ser Gln Arg Lys Ile Pro Ala Lys Val Val Arg Ser Tyr
             35                  40                  45

Arg Lys Gln Glu Pro Ser Leu Gly Cys Ser Ile Pro Ala Ile Leu Phe
     50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95

Gln Lys Pro Ala Gln Gly Cys Arg Lys Asp Arg Gly Ala Ser Lys Thr
             100                 105                 110

Gly Lys Lys Gly Lys Gly Ser Lys Gly Cys Lys Arg Thr Glu Arg Ser
             115                 120                 125

Gln Thr Pro Lys Gly Pro
         130
```